United States Patent [19]

Rule et al.

[11] Patent Number: 4,814,526

[45] Date of Patent: Mar. 21, 1989

[54] SELECTIVE ADSORPTION/SEPARATION OF DIIODONAPHTHALENES

[75] Inventors: Mark Rule; H. L. Browning, Jr., both of Kingsport, Tenn.

[73] Assignee: Eastman Kodak Company, Rochester, N.Y.

[21] Appl. No.: 78,665

[22] Filed: Jul. 28, 1987

[51] Int. Cl.$^4$ .............................................. C07C 17/38
[52] U.S. Cl. .................................. 570/211; 570/206; 570/208
[58] Field of Search ............... 570/202, 203, 206, 208, 570/211

[56] References Cited

U.S. PATENT DOCUMENTS

| | | | |
|---|---|---|---|
| 2,958,708 | 11/1960 | Fleck et al. | 570/211 |
| 3,663,638 | 5/1972 | Neuzil | 570/211 |
| 4,240,987 | 12/1980 | Martin et al. | 570/206 |
| 4,254,062 | 3/1981 | Wambach et al. | 570/211 |
| 4,605,799 | 8/1986 | Miwa et al. | 570/211 |

FOREIGN PATENT DOCUMENTS 159496  1/1964  U.S.S.R. ............................. 570/206

*Primary Examiner*—Werren B. Lone
*Attorney, Agent, or Firm*—Charles R. Martin; William P. Heath, Jr.

[57] ABSTRACT

A process for the separation of a mixture of diiodonaphthalene isomers into an adsorbed component and a non-adsorbed component by passing the mixture over a zeolite to obtain an adsorbed zeolite containing the adsorbed component, separating off the non-adsorbed component and eluting the adsorbed zeolite with a desorbent to obtain the adsorbed component.

18 Claims, No Drawings

SELECTIVE ADSORPTION/SEPARATION OF DIIODONAPHTHALENES

BACKGROUND OF THE INVENTION

1. Field of the Invention

The invention relates to an adsorption/desorption method for the selective separation of diiodonaphthalene isomers.

2. Discussion of the Background

It is well known that isomers of hydrocarbons can be separated by the use of certain adsorbent/desorbent systems. For example, U.S. Pat. No. 3,663,638 discloses the use of zeolite adsorbents for the separation of xylene isomers.

The fundamental operations which occur during the adsorption/desorption process can be described as follows.

(1) In the adsorption step, a feed solution containing a mixture of hydrocarbon isomers is contacted with an adsorbent which selectively adsorbs one or more of the isomers. The unadsorbed or raffinate phase produced by the initial adsorption step is enriched in the isomers which are not adsorbed. The raffinate phase may be concentrated to obtain these less adsorbed species.

(2) In the desorption step, the selectively adsorbed component or components are displaced from the adsorbent by washing the absorbent with a desorbent and recovering the desorbed isomers in the extract stream. The adsorbent is then ready for another cycle of adsorption.

The adsorbent used in the adsorption/separation process must have the ability to selectively adsorb one or more components relative to the remaining components in the mixture. On the other hand, the adsorbent must be able to release the adsorbed components in the presence of a desorbent during the desorption step. Additionally, since the adsorbent will be recycled, the desorbent must be able to be displaced during the following adsorption step by the selectively adsorbed component in the feed mixture to allow the continuous use of the adsorbent in a cyclic manner.

In other words, the adsorbent must more strongly adsorb one component from the mixture relative to the other possible isomers in the feed mixture. The desorbent must be capable of displacing the more selectively adsorbed component and yet be displaced itself by the next adsorption process. Consequently, in the adsorption step there is a competitive adsorption between the more selectively adsorbed component and the desorbent.

These relationships between the adsorbent, desorbent and adsorbed species dictate that a specific adsorbent/desorbent pair be chosen for any particular mixture of isomers which are desired to be separated. This choice is governed by the specific type of adsorbent, chemical structure and properties of the isomers to be separated and properties of the desorbing solvents themselves.

U.S. Pat. No. 2,958,708 discloses the separation of brominated and chlorinated aromatic compounds using adsorbents which are crystalline zeolites. The preferred desorbent is chlorobenzene. U.S. Pat. No. 4,254,062 teaches the use of X or Y type zeolites to separate isomeric di-chlorotoluenes. 2,6-; 2,5-; and 2,4-dichlorotoluenes can be separated from a single mixture using a hydrocarbon desorbent or auxiliary such as decalin, benzene or toluene. U.S. Pat. No. 4,605,799 discloses the separation of halogenated toluene isomers using a Y-type zeolite as the adsorbent and an alkyl aromatic hydrocarbon, 3,4-dihalotoluene or 4-halo-orthoxylene as the desorbent.

The adsorption/desorption processes of the prior art are useful for separating chloro and bromo derivatives of aromatic compounds. Processes which are useful for the separation of iodoaromatic derivatives, and particularly diiodonaphthalenes have not been described.

Accordingly, a need exists for an adsorption/desorption process for separating diiodonaphthalenes economically and on a commercial scale.

SUMMARY OF THE INVENTION

Accordingly, one object of the present invention is to provide a method for the separation of a mixture of diiodonaphthalenes using an adsorption/desorption system.

A further object of the invention is to provide a liquid phase adsorption/desorption system for the separation of a mixture of diiodonaphthalenes.

Still a further object of the present invention is to provide a method for the selective adsorption/desorption of 2,6-diiodonaphthalene and 2,7-diiodonaphthalene.

These and other objects of the present invention which will become apparent from the following specification have been achieved by the present process for the separation of isomeric diiodonaphthalenes into an adsorbed component and a non-adsorbed component, comprising the steps of:

(1) contacting a mixture of isomeric diiodonaphthalenes with a non-acid zeolite to produce a zeolite containing the adsorbed component;

(2) separating off the non-adsorbed component; and (3) eluting the adsorbed component from said zeolite by contacting the adsorbed zeolite with an aromatic hydrocarbon desorbent.

DETAILED DESCRIPTION OF THE PREFERRED EMBODIMENTS

The present method involves the separation of a mixture of diiodonaphthalene isomers. The isomer mixture may be prepared by any known process, such as for example iodination or oxyiodination reactions. Suitable iodination reactions include liquid phase iodinations utilizing iodine and nitric acid or other strong acids and/or use strong oxidants such as ozone, persulfates, etc. such as those disclosed in U.S. Pat. No. 4,240,987. The isomer mixture is preferably produced by the oxyiodination of naphthalene. Preferred processes for producing the isomer mixture from an oxyiodination reaction of naphthalene are disclosed in co-pending U.S. application Ser. Nos. 912,806 filed Sept. 29, 1986; 029,959 filed Mar. 25, 1987; 029,898 filed Mar. 25, 1987; 029,897 filed Mar. 25, 1987; and 029,896 filed Mar. 25, 1987. The disclosures of these applications are incorporated herein by reference for a more complete description of these oxyiodination reactions and processes.

Additionally, the isomer mixture may be prepared by the isomerization or transiodination reaction of an oxyiodination product which has previously been prepared. The isomerization or transiodination reactions effectively redistribute the iodine among the aromatic species thereby increasing the yield of one or more specific isomers. Preferred isomerization or transiodination processes which may be used to produce the isomer mixture are disclosed in copending U.S. application Ser.

Nos. 029,899, filed Mar. 25, 1987; 029,956, filed Mar. 25, 1987; and 029,949, filed Mar. 25, 1987. The disclosures of these applications are incorporated herein by reference for a more complete description of these isomerization and transiodination reactions. While the processes as noted above are preferred processes for preparing the initial isomer mixtures, any process which produces diiodonaphthalene isomers may be used to produce the initial isomer mixture.

Some diiodonaphthalene isomers can be readily separated by fractional crystallization. However, some of the isomers including the 2,6- and 2,7-isomers, have similar solubilities and are therefore difficult to separate by fractional crystallization in high yield except when one of the isomers is present in a large excess relative to the other. Moreover, since the typical oxyiodination catalysts produce a product with a 2,6/2,7 ratio greater than 1, it is not possible to obtain pure 2,7-diiodonaphthalene by fractional crystallization.

It has now been found that diiodonaphthalene isomers can be readily separated by selective adsorption/desorption on a number of zeolitic materials. These zeolites are the same zeolites as those used as catalysts in the oxyiodination processes of the co-pending applications noted above. Preferably, 13X zeolite is used as the adsorbent, and more preferably a 13X zeolite which has been exchanged with sodium or potassium ions. Use of these adsorbents allows one to obtain high yields of pure isomers, particularly 2,6- and 2,7-diiodonaphthalenes, regardless of the initial 2,6/2,7 ratio.

The desorbent is preferably an aromatic hydrocarbon such as, for example, benzene, a xylene, toluene or naphthalene. Preferred desorbents are the xylenes, toluene and naphthalene, with ortho-, meta-, and para-xylene being more preferred. The most preferred desorbent is ortho-xylene.

The adsorptive/desorption separation can be conducted over a wide range of temperatures. The temperature of operation is governed by the solubility of the isomers in the desorbent, and must be selected so that all isomers remain soluble. Satisfactory results have been obtained at temperatures between about 0°-200° C., with temperatures of operation being preferably in the range of about 80°-150° C.

The adsorption separation process can be operated at any pressure at which the isomers and desorbent are liquid and will depend on the rate at which the desorbent can be forced through the adsorbent bed or column. Typical pressures are those ranging from ambient or atmospheric pressure to about 50,000 psi. The adsorption/desorption process may also be operated in a vapor phase process. However, the low vapor pressure of the diiodonaphthalenes and the resulting high temperature requirements make this a less preferred embodiment of this invention.

The adsorbent may be contained in any apparatus customarily used for continuous or batchwise separation by adsorption. Accordingly, the adsorbent may be charged into an adsorption column, or may be present in a fixed, moving, or fluid bed. In a preferred embodiment, the adsorption catalyst is present in a fixed bed configuration.

The isomer mixture is first passed onto the bed to allow selective adsorption. The non-adsorbed isomers are collected and processed as they exit the adsorption bed. The adsorbed isomers are then washed off the bed by means of the desorbent and collected in the elutant stream for processing.

Of course, the process can be run in a discontinuous or batchwise manner.

When a mixture containing 2,6- and 2,7-diiodonaphthalenes are separated by the adsorption/desorption system of the present invention 2,7-diiodonaphthalene and other diiodonaphthalenes are selectively adsorped onto the adsorption bed. 2,6-diiodonaphthalene is the least adsorped species and passes through the adsorbent bed first, 2,7-diiodonaphthalene is the next least strongly adsorbed isomer and is eluted next, followed by other diiodonaphthalene isomers. Carbonylation of the obtained pure diiodonaphthalene isomers yield the corresponding acid or ester. 2,6-naphthalene dicarboxylic acid and its esters are particularly desired for use in the manufacture of polyesters which have excellent barrier properties and can be fabricated into films, bottles, or coatings.

The zeolite adsorbent preferably has a particle size of between 0.1 and 20 mm, preferably 0.2–10 mm. The particle size of the zeolite is not critical, although smaller particle sizes will necessitate the use of higher pressures in the separation system.

Flow rates through the separation system will depend on the geometry of the adsorbent beds and the particle size of the adsorbent, as well as the separation profile for the individual compounds desired to be separated.

The adsorption/desorption separation bed may be located immediately downstream from an iodination, oxyiodination or transiodination reactor and therefore is capable of directly accepting the reaction products from these reactors. It is both economical and surprising that the side-products from these reactors do not affect the separation capacity of the adsorption/desorption separation system.

Other features of the invention will become apparent in the course of the following descriptions of exemplary embodiments which are given for illustration of the invention are are not intended to be limiting thereof.

EXAMPLES 1–10

In the following table, the results of competitive adsorption of mixed diiodonaphthalenes on different zeolites are presented and compared with the traditional adsorbents alumina and silica. In all examples, 5.0 grams of adsorbent, 1.0 grams of mixed diiodonaphthalenes, and 6.0 grams of o-xylene were mixed and heated on a steam bath for 30 minutes at 80° C. The raffinate was then removed and the adsorbent washed quickly with 2 grams of o-xylene. The adsorbed species were then removed by desorption with toluene at 80° C. for 30 minutes and both fractions were analyzed by gas chromatography. The relative adsorption selectivity was calculated by the standard formula: alpha=(2,7-adsorbed/2,7-raffinate)/(2,6-adsorbed/2,6-raffinate)

TABLE 1

| Results of Competitive Adsorption | | |
|---|---|---|
| Adsorbent | alpha | grams adsorbed |
| Na—X | 3.42 | 0.31 |
| K—Y | 2.10 | 0.37 |
| Na—Y | 1.07 | 0.23 |
| K—X | 2.76 | 0.30 |
| Zeolon-Na | 1.38 | 0.10 |
| Li—X | 1.44 | 0.31 |
| Cs—X | 1.49 | 0.26 |
| K—Ba—X | 1.69 | 0.28 |
| alumina | 1.00 | 0.04 |
| silica | 1.00 | 0.02 |

On all zeolites tested, the 2,6-diiodonaphthalene is the least adsorbed species, and therefore is present in the raffinate. Superior separation is indicated by a high alpha value, which an alpha value of 1.0 indicates no relative separation.

EXAMPLE 11-13

In each of the following examples a 10 wt % solution of diiodonaphthalenes in p-xylene was injected onto an Ana-Prep liquid chromatograph fitted with the indicated column and eluted with p-xylene. Eluted fractions were collected and analyzed for 2,6-diiodonaphthalene, 2,7-diiodonaphthalene, 2-iodonaphthalene, and other diiodonaphthalenes.

EXAMPLE 11

| DIN composition: | 5.6% 2-In, 26.4% 2,7 DIN, 65.9% 2,6 DIN |  |
|---|---|---|
| Column temp: | 135 deg C. |  |
| Column packing: | K—X beads (16–40 mesh), 1" × 4' column |  |
| Injection volume: | 200 ml |  |

| Fraction No. | %2,6 | %2,7 |
|---|---|---|
| 1 | 100.0 | 0.0 |
| 2 | 90.3 | 9.7 |
| 3 | 81.0 | 19.0 |
| 4 | 65.0 | 35.0 |
| 5 | 46.0 | 54.0 |
| 6 | 30.0 | 70.0 |
| 7 | 0.0 | 100.0 |
| 8 | 0.0 | 0.0 |
| 9 | 0.0 | 0.0 |

EXAMPLE 12

| DIN composition: | 48.2% 2-In, 19.8% 1-IN, 6.8% 2,7 DIN, 12.3% 2,6 DIN, 9.0% other DIN's |
|---|---|
| Column temp: | 133 deg C. |
| Column packing: | Na—X powder (2 micrometer diameter), 2.5" × 3' column |
| Injection volume: | 500 ml |

| Fraction No. | %2,6 | %2,7 | %2-IN | % Other DIN's |
|---|---|---|---|---|
| 1 | 0.0 | 0.0 | 0.0 | 0.0 |
| 2 | 61.0 | 0.0 | 39.0 | 0.0 |
| 3 | 56.2 | 0.0 | 43.8 | 0.0 |
| 4 | 51.0 | 0.0 | 49.0 | 0.0 |
| 5 | 30.3 | 47.0 | 22.3 | 0.0 |
| 6 | 28.4 | 53.8 | 17.8 | 0.0 |
| 7 | 0.0 | 0.0 | 5.2 | 94.8 |
| 8 | 0.0 | 0.0 | 0.0 | 100.0 |
| 9 | 0.0 | 0.0 | 0.0 | 100.0 |
| 10 | 0.0 | 0.0 | 0.0 | 100.0 |
| 11 | 0.0 | 0.0 | 0.0 | 100.0 |
| 12 | 0.0 | 0.0 | 0.0 | 0.0 |

EXAMPLE 13

| DIN composition: | 22.1% 2-In, 5.7% 1-IN, 28.2% 2,6 DIN, 43.0% 2,7 DIN |  |
|---|---|---|
| Column temp: | 140 deg C. |  |
| Column Packing: | K—X powder (2 micrometer diameter), 3" × 3' column |  |
| Injection volume: | 150 ml |  |

| Fraction No. | %2,6 | %2,7 | %2-IN |
|---|---|---|---|
| 1 | 100.0 | 0.0 | 0.0 |
| 2 | 100.0 | 0.0 | 0.0 |
| 3 | 100.0 | 0.0 | 0.0 |
| 4 | 100.0 | 0.0 | 0.0 |
| 5 | 24.9 | 75.1 | 0.0 |
| 6 | 8.7 | 91.3 | 0.0 |
| 7 | 0.0 | 100.0 | 0.0 |
| 8 | 0.0 | 100.0 | 0.0 |
| 9 | 0.0 | 100.0 | 0.0 |
| 10 | 0.0 | 100.0 | 0.0 |
| 11–20 | 0.0 | 0.0 | 100.0 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the separation of an iodonaphthalene isomer selected from the group consisting of 2,6-diiodonaphthalene, 2,7-diiodonaphthalene and 2-iodonaphthalene from a mixture of diiodonaphthalene isomers containing said iodonaphthalene isomer into an adsorbed component and a non-adsorbed component, comprising the steps of:

(i) contacting said mixture of isomeric diiodonaphthalenes with a non-acid zeolite to produce an adsorbed zeolite containing said adsorbed component, (ii) separating off said non-adsorbed component at a temperature between about 0°-200° C. to obtain said non-adsorbed component;

(iii) eluting said adsorbed component from said adsorbed zeolite with an aromatic hydrocarbon desorbant to obtain said adsorbed component; and (iv) isolating said iodonaphthalene isomer from said adsorbed component or said non-adsorbed component.

2. The method of claim 1, wherein said desorbent is selected from the group consisting of o-xylene, m-xylene, p-xylene, toluene and naphthalene.

3. The method of claim 2, wherein said desorbent is o-xylene.

4. The method of claim 1, wherein said separating step is conducted at temperatures between about 80°-150° C.

5. The method of claim 1, wherein said adsorbed component is 2,7-diiodonaphthalene and said non-adsorbed component is 2,6-diiodonaphthalene.

6. The method of claim 1, wherein said zeolite is a 13X zeolite.

7. The method of claim 6, wherein said zeolite is a 13X zeolite exchanged with sodium or potassium ions.

8. A method for the preparation and separation of an iodonaphthalene isomer selected from the group consisting of 2,6-diiodonaphthalene, 2,7-diiodonaphthalene and 2-iodonaphthalene from a mixture of diiodonaphthalene isomers containing said iodonaphthalene isomer into an adsorbed component and a non-adsorbed component, comprising the steps of:

(i) reacting iodine with naphthalene to produce a mixture of diiodonaphthalene isomers;

(ii) contacting said mixture with a non-acid zeolite to produce an adsorbed zeolite containing said adsorbed component;

(iii) separating off said non-adsorbed component at a temperature between about 0°-200° C. to obtain said non-adsorbed component;

(iv) eluting said adsorbed component from said adsorbed zeolite with an aromatic hydrocarbon desorbent to obtain said adsorbed component; and (v) isolating said iodonaphthalene isomer from said adsorbed component or said non-adsorbed component.

9. The method of claim 9, wherein said desorbent is selected from the group consisting of o-xylene, m-xylene, p-xylene, toluene and naphthalene.

10. The method of claim 9, wherein said desorbent is o-xylene.

11. The method of claim 8, wherein said separating step is conducted at a temperature between about 80°–150° C.

12. The method of claim 8, wherein said adsorbed component is 2,7-diiodonaphthalene and said non-adsorbed component is 2,6-diiodonaphthalene.

13. The method of claim 8, wherein said zeolite is a 13X zeolite.

14. The method of claim 13, wherein said zeolite is a 13X zeolite exchanged with sodium or potassium ions.

15. The method of claim 8, wherein said reacting step comprises an oxyiodination reaction.

16. The process of claim 15, wherein said oxyiodination reaction comprises reacting a source of iodine with naphthalene in the presence of a source of molecular oxygen and a zeolite catalyst to produce a mixture of diiodonaphthalene isomers.

17. The method of claim 8, further comprising the step of isomerizing said mixture of diiodonaphthalene isomers prior to said contacting step.

18. The method of claim 17, wherein said isomerizing step comprises contacting said mixture of diiodonaphthalene isomers with a zeolite catalyst.

* * * * *